(12) United States Patent
Yamaguchi et al.

(10) Patent No.: US 8,010,223 B2
(45) Date of Patent: Aug. 30, 2011

(54) QUALITY CONTROL SYSTEM AND QUALITY CONTROL INFORMATION DELIVERY DEVICE

(75) Inventors: Tadayuki Yamaguchi, Kobe (JP); Minoru Takayanagi, Kobe (JP); Takeshi Matsumoto, Kasai (JP); Tamiko Fujita, Akashi (JP)

(73) Assignee: Sysmex Corporation, Kobe (JP)

( * ) Notice: Subject to any disclaimer, the term of this patent is extended or adjusted under 35 U.S.C. 154(b) by 46 days.

(21) Appl. No.: 11/788,791

(22) Filed: Apr. 20, 2007

(65) Prior Publication Data

US 2008/0021572 A1    Jan. 24, 2008

(30) Foreign Application Priority Data

Apr. 21, 2006 (JP) ................ 2006-118522

(51) Int. Cl.
  *G06F 19/00* (2006.01)
  *G06Q 10/00* (2006.01)
  *G01N 33/48* (2006.01)
  *G01N 31/00* (2006.01)
(52) U.S. Cl. ............ 700/170; 705/5; 702/19; 702/31
(58) Field of Classification Search ............ 700/170; 705/3; 702/19, 31
  See application file for complete search history.

(56) References Cited

U.S. PATENT DOCUMENTS

| | | | |
|---|---|---|---|
| 4,858,154 A | 8/1989 | Anderson et al. | |
| 4,953,075 A * | 8/1990 | Nau et al. | 700/17 |
| 5,199,439 A * | 4/1993 | Zimmerman et al. | 600/483 |
| 5,532,941 A | 7/1996 | Lin | |
| 5,835,384 A | 11/1998 | Lin | |
| 6,629,060 B2 | 9/2003 | Okuno et al. | |
| 6,678,355 B2 * | 1/2004 | Eringis et al. | 379/22 |
| 6,766,283 B1 * | 7/2004 | Goldman et al. | 703/2 |
| 6,937,964 B2 | 8/2005 | Okuno et al. | |
| 7,031,986 B2 * | 4/2006 | Ito | 707/204 |
| 7,072,800 B1 * | 7/2006 | Fernandez et al. | 702/186 |
| 7,152,067 B2 * | 12/2006 | Yagawa et al. | 707/10 |
| 7,229,409 B2 * | 6/2007 | Ito et al. | 600/300 |
| 7,490,046 B1 * | 2/2009 | Wyatt | 705/2 |
| 7,509,263 B1 * | 3/2009 | Fiedotin et al. | 705/3 |
| 7,624,028 B1 * | 11/2009 | Brown | 705/3 |
| 2003/0009295 A1 * | 1/2003 | Markowitz et al. | 702/20 |
| 2003/0154044 A1 * | 8/2003 | Lundstedt et al. | 702/104 |
| 2003/0213902 A1 * | 11/2003 | Takahashi | 250/282 |
| 2004/0024293 A1 * | 2/2004 | Lawrence et al. | 600/300 |
| 2004/0220761 A1 | 11/2004 | Yundt-Pacheco | |
| 2005/0172212 A1 * | 8/2005 | Birsa et al. | 715/500 |
| 2006/0184264 A1 * | 8/2006 | Willis et al. | 700/108 |
| 2007/0116037 A1 * | 5/2007 | Moore | 370/462 |
| 2008/0046292 A1 * | 2/2008 | Myers et al. | 705/3 |
| 2008/0097794 A1 * | 4/2008 | Arnaud et al. | 705/3 |
| 2008/0319829 A1 * | 12/2008 | Hunt et al. | 705/10 |

OTHER PUBLICATIONS

Lemkin et al., "The Protein Disease Database of Human Body Fluids: II. Computer Methods and Data Issues" Electrophoresis Society, 1995, p. 55-72.*

* cited by examiner

*Primary Examiner* — Ramesh B Patel
*Assistant Examiner* — Thomas Stevens
(74) *Attorney, Agent, or Firm* — Brinks Hofer Gilson & Lione (57) ABSTRACT

There is provided a quality control system capable of displaying a display screen regarding quality control of an testing, including a display control part for performing a display control of the display screen regarding the quality control, wherein the display control part displays the display screen on a display in accordance with a category of a quality control sample used by a user.

14 Claims, 9 Drawing Sheets

QUALITY CONTROL SYSTEM AND QUALITY CONTROL INFORMATION DELIVERY DEVICE

RELATED APPLICATIONS

This application claims priority under 35 U.S.C. §119 to Japanese Patent Application No. JP2006-118522 filed Apr. 21, 2006, the entire content of which is hereby incorporated by reference.

FIELD OF THE INVENTION

The present invention relates to a quality control system and a quality control information delivery device.

BACKGROUND

In a clinical examination such as a blood test and a biochemical test, quality control is important to secure reliability of a test. The quality control is performed by measuring a quality control sample (also called a quality control material) same as a biological substance or similar to the biological substance, and monitoring its measurement result. This quality control includes a method of monitoring whether or not a stable measurement result is obtained by measuring the same quality control sample every day at the same facility (internal quality control), and a method of aggregating the measurement results of the quality control sample at a plurality of facilities and performing the quality control (external quality control).

In the case of performing the external quality control, for example, quality control data sent from the plurality of facilities is aggregated by classifying it per each quality control sample, and a population per each quality control sample is formed. Then, in each facility, a difference between an average of the quality control data of an overall population and the quality control data of this facility is monitored.

Here, the external quality control needs to collect the quality control data from the plurality of facilities and aggregate such collected data. Therefore, collection of the quality control data is performed through a network. The quality control system using the network is disclosed, for example, in U.S. Pat. Nos. 6,937,964 and 6,629,060 and International Publication No. WO2002/052278.

The external quality control is not necessarily performed uniformly. Namely, there are various methods for aggregating the quality control data and viewing methods of the quality control results. For example, a method of obtaining an average value of the quality control data (measurement value of the quality control sample) sent from the plurality of facilities includes a method of calculating an average value directed to only the data of the day, and a method of calculating an average value directed to the data generated in a fixed period of time. In addition, the quality control sample also includes an exclusive sample for a particular testing device or a general purpose sample for any testing device irrespective of a manufacturer and a model as far as the testing device is used in a certain testing field. Further, when the quality control result is viewed, different display methods are employed depending on the aggregating method and the kind of the quality control sample.

However, conventionally, there exists no system capable of handling a plurality of different methods relating to quality control. Meanwhile, when a system capable of performing the quality control by a plurality of methods is constructed, the system becomes complicated and convenience and operability of the system may be deteriorated. Accordingly, in such a case also, new technical means is desired to prevent the deterioration of the convenience and the operability of the system.

SUMMARY

The scope of the present invention is defined solely by the appended claims, and is not affected to any degree by the statements within this summary.

A first aspect of the present invention is to provide a quality control system comprising a user terminal. The user terminal comprises an input device for receiving an input of information, a first communication device for communicating with an apparatus via a network and a display device for displaying a screen. The quality control system also comprises a quality control server. The quality control server comprises a second communication device for communicating with an apparatus via the network.

The user terminal further comprises first communication control means for controlling the first communication device to transmit an identifying information for identifying a quality control sample, when the input device receives an input of the identifying information.

The quality control server further comprises second communication control means for controlling the second communication device to transmit first screen information for displaying a first screen regarding the quality control sample belonging to a first category, when the second communication device receives the identifying information which identifies the quality control sample belonging to the first category.

The quality control server also comprises third communication control means for controlling the second communication device to transmit second screen information for displaying a second screen regarding the quality control sample belonging to a second category, when the second communication device receives the identifying information which identifies the quality control sample belonging to the second category.

The user terminal further comprises first display control means for controlling the display device to display the first screen based on the first screen information, when the first screen information is received by the first communication device, and second display control means for controlling the display device to display the second screen based on the second screen information, when the second screen information is received by the first communication device.

A second aspect of the present invention is to provide a quality control system comprising an analyzer for analyzing a sample and a quality control server for supplying a quality control result.

The analyzer comprises analyzing means for analyzing a sample, a first communication device for communicating with the quality control server and analysis result transmitting means for controlling the first communication device to transmit an analysis result of a quality control sample, when the quality control sample is analyzed by the analyzing means.

The quality control server comprises a second communication device for communicating with the analyzer and determination means for determining whether the analysis result received by the second communication device is a first analysis result of the quality control sample belonging to a first category, or a second analysis result of the quality control sample belonging to a second category, when the second communication device receives the analysis result.

The quality control server further comprises a storage device comprises a first database and a second database, first writing means for writing the analysis result to the first database, when the analysis result is determined to be the first analysis result by the determination section and second writing means for writing the analysis result to the second database, when the analysis result is determined to be the second analysis result by the determination section.

A third aspect of the present invention is to provide a quality control information delivery device comprising a communication device for communicating with an external apparatus and receiving means for controlling the communication device to receive request information including identifying information for identifying a quality control sample, the request information for requesting the information used for displaying a screen regarding the quality control sample identified by the identifying information.

The quality control information delivery device further comprises first transmitting means for controlling the communication device to transmit first screen information for displaying a first screen regarding the quality control sample belonging to a first category, when the identifying information included in the request information received by the communication device is the information for identifying the quality control sample belonging to the first category, and second transmitting means for controlling the communication device to transmit second screen information for displaying a second screen regarding the quality control sample belonging to a second category, when the identifying information included in the request information received by the communication device is the information for identifying the quality control sample belonging to the second category.

A fourth aspect of the present invention is to provide a quality control information delivery device comprising a communication device for communicating with an analyzer for analyzing a sample and determination means for determining whether an analysis result of a quality control sample received by the communication device is a first analysis result of the quality control sample belonging to a first category, or a second analysis result of the quality control sample belonging to a second category, when the communication device receives the analysis result from the analyzer.

The quality control information delivery device further comprises a storage device comprises a first database and a second database, first writing means for writing the analysis result to the first database, when the analysis result is determined to be the first analysis result by the determination section and second writing means for writing the analysis result to the second database, when the analysis result is determined to be the second analysis result by the determination section.

DETAILED DESCRIPTION OF THE EMBODIMENTS

Hereunder, embodiments of the present invention will be explained in detail, with reference to the appended drawings.
[Service Outline Provided by System]

Figure 1:
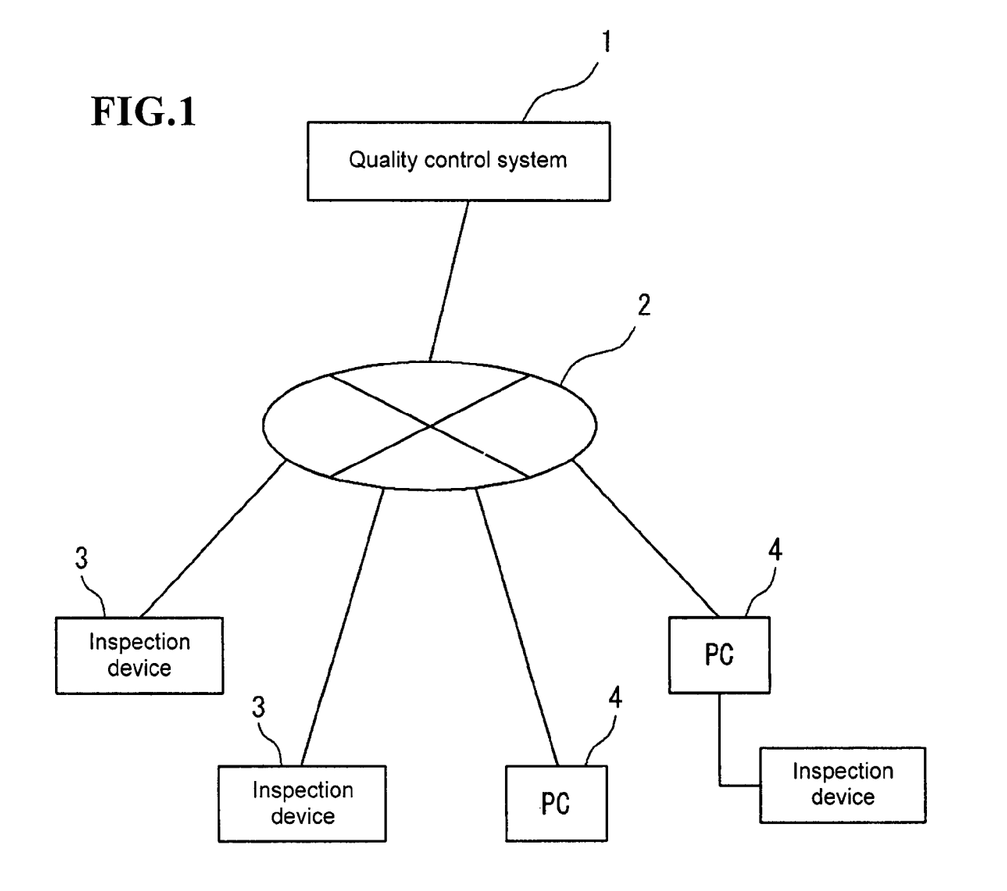
FIG. 1 is a configuration diagram of a network of a quality control system.

As shown in FIG. 1, a quality control system according to an embodiment includes a quality control server 1, an analyzing device 3 and a user terminal (computer) 4 connected to the quality control server 1 through a network such as internet 2. The quality control server 1 can be used from the analyzing device 3 and the user terminal 4 through the internet 2.

This quality control system functions to perform an external quality control of a clinical examination, and based on quality control data sent from a plurality of inspection facilities through the network 2, performs the external quality control. The external quality control is performed in such a way that result data obtained by measuring a quality control sample (also called "control material") by an inspection device is sent to the quality control server 1 as quality control data, which is then aggregated in the quality control server 1.

In the system of this embodiment, the quality control sample, being a quality control object, is classified into two kinds (a plurality of kinds) of categories. An exclusive quality control sample belongs to a first category, which is sold as an exclusive sample of each device of a prescribed inspection device such as a hemocyte analytical device, a blood coagulation measuring device, and a urine measuring device. A general-purpose type quality control sample belongs to a second category, which is the quality control sample used in a field of an inspection such as biochemistry, blood serum, glycohemoglobin, virus, infection diseases, and blood coagulation, irrespective of the kind of the device in which the quality control sample is used (a device of other manufacturer may be allowed).
[Hardware Structure of Quality Control Server 1]

Figure 2:
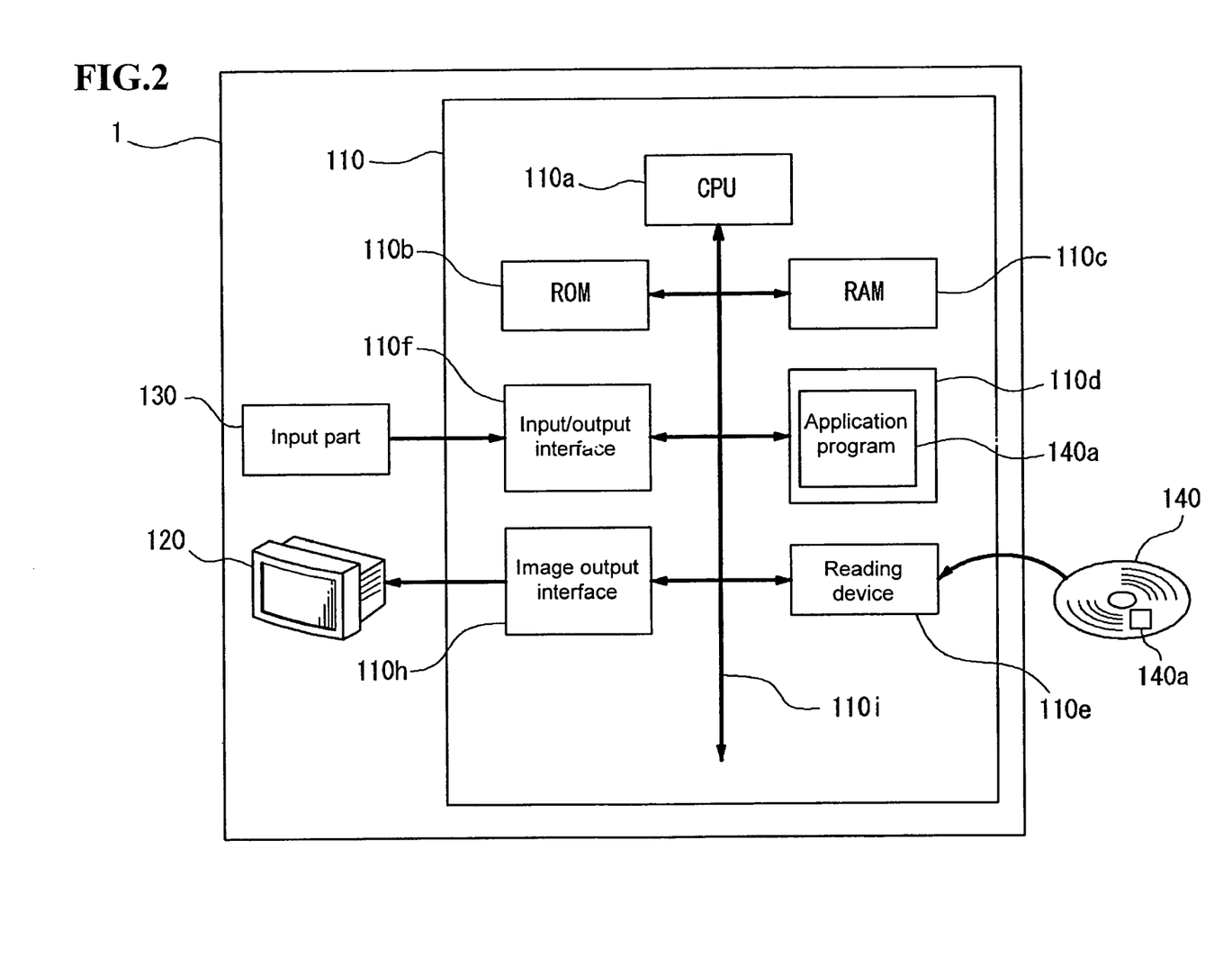
FIG. 2 is a configuration diagram of hardware of the quality control system.

FIG. 2 is a block diagram showing a hardware structure of the quality control server 1. The quality control server 1 is constituted of a computer mainly composed of a main body 110, a display 120, and an input device 130.

The main body 110 is mainly constituted of a CPU 110a, ROM 110b, RAM 110c, a hard disk 110d, a reading device 110e, an input/output interface 110f, and an image output interface 110h. The CPU 110a, ROM 110b, RAM 110c, hard disk 110d, reading device 110e, input/output interface 110f, and image output interface 110h are connected by a bus 110i so as to be able to communicate data.

The CPU 110a can execute a computer program stored in the ROM 110b and a computer program loaded on the RAM 110c. Then, by executing an application program 140a by the CPU 110a, each functional block as will be described later is realized, and the computer functions as the quality control server 1.

The ROM 110b is constituted of a mask ROM, PROM, EPROM, EEPROM and the like, and the computer program executed by the CPU 110a and data and the like used in this computer program are recorded in the ROM 110b.

The RAM 110c is constituted of SRAM or DRAM, and the like. The RAM 110c is used for reading the computer program recorded in the ROM 110b and the hard disk 110d. In addition, when these computer programs are executed, the RAM 110c is used as a working area of the CPU 110a.

Various computer programs to be executed by the CPU 110a and data used for executing these computer programs such as an operating system, an application program and the like are installed on the hard disk 110d. The application program 140a is also installed on this hard disk 110d.

The reading device 110e is constituted of a flexible disk drive, a CD-ROM drive, or a DVD-ROM drive and the like, and is capable of reading the computer program or data recorded in a portable recording medium 140. In addition, the application program 140a for making the computer function as the system of the present invention is stored in the portable recording medium 140, and it is possible for the computer to read the application program 140a of the present invention from this portable recording medium 140 and install this application program 140a on the hard disk 110d.

In addition, the application program 140a is not only provided by the portable recording medium 140 but can be provided through an electric communication line from an external, equipment communicatively connected with the computer by the electric communication line (irrespective of wired or wireless line). For example, it is possible that the application program 140a is stored in the hard disk of the server computer on the internet, the computer 100a accesses this server computer, downloads this computer program, and installs this computer program on the hard disk 110d.

In addition, an operating system for providing a graphical user interface environment such as Windows® manufactured and sold by US Microsoft Corporation is installed on the hard disk 110d. In an explanation given hereunder, the application program 140a according to this embodiment is operated on this operating system.

The input/output interface 110f is constituted of, for example, a serial interface such as USB, IEEE1394, RS-232C, a parallel interface such as SCSI, IDE, IEEE1284, and an analog interface composed of a D/A converter, an A/C converter and the like. The input device 130 composed of a keyboard and a mouse is connected to the input/output interface 110f, and by using this input/output device 130 by a user, the data can be inputted in the computer 100a.

The display 120 composed of LCD or CRT and the like is connected to the image output interface 110h, thereby outputting an image signal corresponding to the image data given from the CPU 110a to the display 120. The display 120 displays the image (screen) in accordance with the image signal thus inputted.

[Function of Quality Control Server 1]

Figure 3:
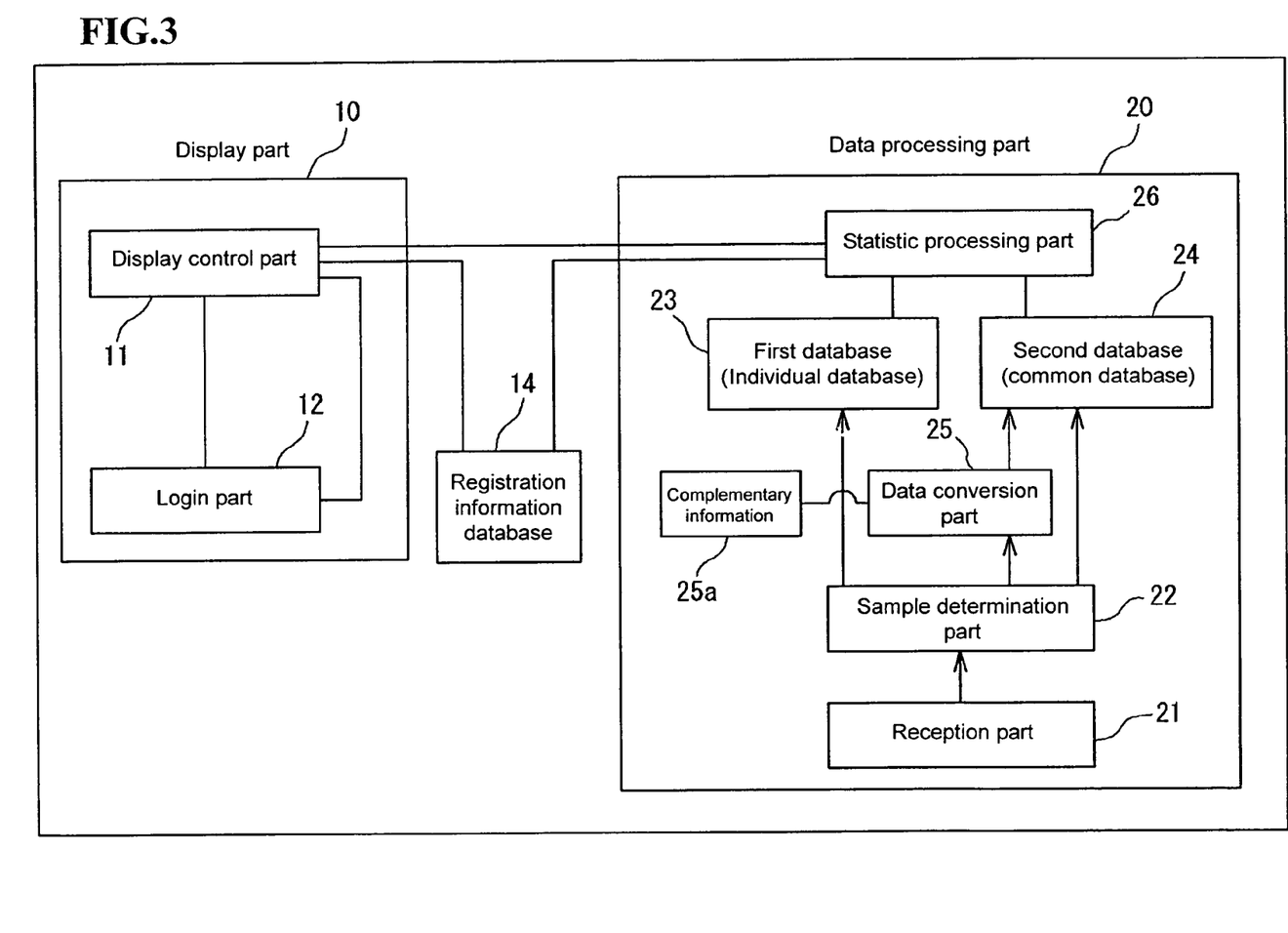
FIG. 3 is a block diagram of a function of the quality control system.

FIG. 3 shows a function block of the quality control server 1. As shown in the figure, the quality control server 1 has a function as a display part (Web server) 10 for displaying a screen (Web page) on a terminal device 4 when the user accesses the system through the internet 2 from the terminal device 4 such as a personal computer, and a function as a data processing part 20 for collecting, accumulating, and processing the quality control data from the personal computer 4 in which the quality control data is transferred from an inspection device or an inspection device 3 of each inspection facility (both of them are generally called an "inspection device and the like" hereunder).

[Display Part 10 of System]

The display part 10 is provided with a display control part 11 for displaying the Web screen such as a display screen of a login screen and a quality control result. For example, when the user accesses the system, the display control part 11 displays the login screen on the user terminal 4 that accessed the quality control server 1. In addition, the display part 10 is provided with a login part 12 for performing a processing for login from a user. If a login name and a password inputted in the login screen are appropriate, the login part 12 allows the login. Note that the login name and the password are given for each inspection facility.

The display control part 11 can perform display control by referring to a registration information database 14, and can display a statistic processing result based on databases 23 and 24 of the data processing part 20. Note that the registration information database 14 is a storage part in which information regarding the user, information of the inspection device possessed by the user, and information regarding a user attribute such as a measurement condition (measurement method and the kind of the sample used) in each inspection device possessed by each user, and other various kinds of information, are registered.

[Data Processing Part 20 of System]

The data processing part 20 has a reception part 21 for receiving the quality control data sent from the inspection device and the like by electronic mail and other data transmitting means. The quality control data is attached to the electronic mail as an attached file described in a prescribed data format, and is transmitted to the quality control server 1 from the inspection device and the like, and is received by the reception part 21. Note that the quality control data may be described in a main body of the electronic mail.

Here, the data format and data items are different between the quality control data of the quality control sample belonging to the first category and the quality control data of the quality control sample belonging to the second category. For example, the former quality control data includes, as the data items, the kind of the inspection device (lot number and density level), the inspection items (numbers of red blood cells and white blood cells in case of hemocyte analytical device), the measurement value of the quality control sample for each inspection item, and the inspection date and time, and the like. Such data is described in an exclusive format for the first category.

In addition, the latter quality control data includes, as the data items, the kind of the inspection device, the inspection items, the measurement value of the quality control sample for each inspection item, the inspection date and time, and the kind of the quality control sample (lot number and density level), and the like. Such data is described in the exclusive format for the second category.

The data processing part 20 is provided with a sample determination part 22 for determining whether the received quality control data is the data for the quality control sample belonging to the first category or the data for the quality control sample belonging to the second category based on the data format of the quality control data. Note that the sample determination part 22 may determine the category based on data kind identification information added to the quality control data. The data determined to be the quality control data of the first category by the sample determination part 22 is accumulated in a first database 23. In addition, the data determined to be the quality control data of the second category by the sample determination part 22 is accumulated in a second database 24. Further, the data determined to be the quality control data of the first category is also accumulated in the second database 24.

In this way, the first database is an individual database in which the quality control data of the quality control sample belonging to the first category is accumulated, and the second database is a common database in which both of the quality control data of the quality control sample belonging to each category are accumulated. Note that in this embodiment, the data format of the second category is adopted as the data format in the common database 24. Therefore, the common database 24 includes the function as the individual database in which the quality control data of the quality control sample belonging to the second category is accumulated. Accordingly, in this embodiment, the individual database in which only the quality control data of the quality control sample belonging to the second category is omitted.

In addition, since the quality control data of the first category is accumulated in the second database for data with a different data format, the quality control data of the first category is converted into the data format of the second category by a data conversion part 25. Further, by partial information omission or the like, in some cases, it is impossible to convert into the second category only with the quality control data of the first category. In this case, in order to surely perform data conversion from the format of the first category to the format of the second category, the data conversion part has a data complementing function (data complementing part). Specifically, when the data needs complementing, the data complementing part of the data conversion part 25 refers to complementary information 25*a* registered for each user, adds the complementary information to the quality control data of the first category, and defines it as the data to be stored in the second database 24.

The data processing part 20 is provided with a statistic processing part 26 for performing statistic processing for quality control, based on the data accumulated in both of the databases 23 and 24. In the display control part 11 of the display part 10, a statistic processing result obtained in the statistic processing part 26 can be displayed on the user terminal as a Web screen.

The statistic processing part 26 is capable of performing a first statistic processing by a first method and a second statistic processing by a second method. In the first statistic processing, based on the first database 23, the measurement result of the sample is aggregated so as to form a population for each kind of sample, thus making it possible to perform the statistic processing for each population. As the first statistic processing, for example, calculation of the average of the quality control data (measurement result of quality control sample) in the population and the calculation of a standard deviation of each quality control data in the population are performed. In addition, in the first statistic processing, the calculation of the average in the population is performed per day. Namely, when an average value of the quality control data of a certain day is calculated, the average value directed to only the quality control data of the day is calculated.

In the second statistic processing, based on the second database, the measurement result of the sample is aggregated so as to form an entire body of the population for each kind of the sample, thus making it possible to execute the statistic processing for each population or selected standard population. In the same way as the first statistic processing, in the second statistic processing, the calculation of the average of the quality control data in the (standard) population, the calculation of the standard deviation of each quality control data in the (standard) population, and the like are performed. In addition, the second statistic processing has more different kinds of statistic processing functions than the first statistic processing. In addition, in the second statistic processing, the average of the quality control data in the population is calculated as the average value of the quality control data in a prescribed period of a plurality of days (effective using period of quality control sample as an object). Namely, in the second statistic processing, the average value of the quality control data of the quality control sample, being the same quality control sample and having the same effective using period of the sample specified by the lot number or the like of the sample is calculated. In this way, statistic processing methods are different from each other between the first statistic processing and the second statistic processing.

[Reception/Accumulation Processing of Quality Control Data]

Figure 4:
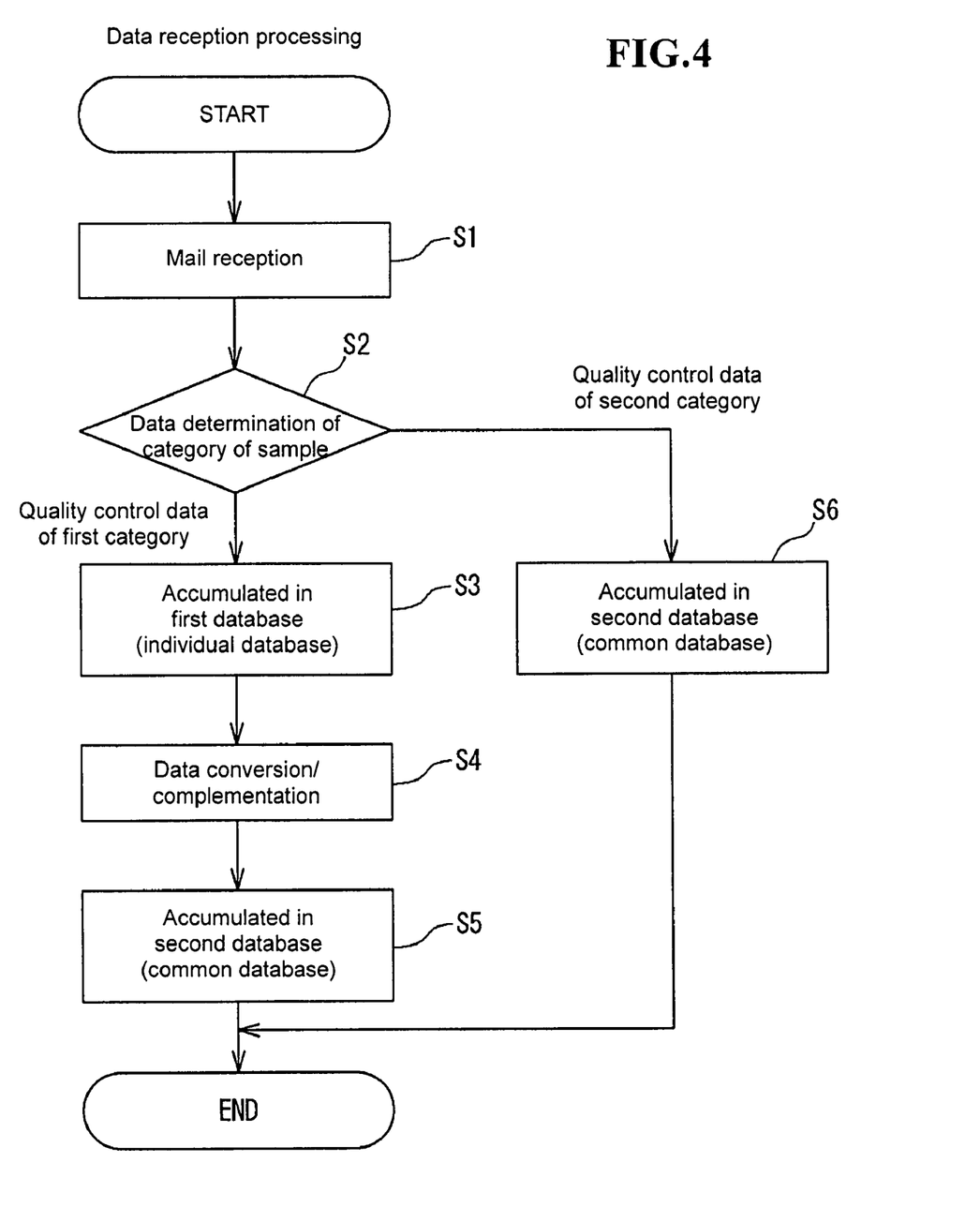
FIG. 4 is a flowchart of a reception processing of quality control data.

FIG. 4 shows the processing regarding the reception of the quality control data transmitted from the analyzing device 3 of the user or the user terminal 4. In addition, when the quality control sample is measured by the analyzing device of the user, the quality control data is immediately or periodically transmitted to the quality control server 1 from the analyzing device and the like by an electronic mail, and the quality control data thus transmitted is received by the reception part 21 of the quality control server 1 (step S1). The quality control server 1 extracts the quality control data from the mail received by the reception part 21, and based on the data format of the quality control data, the sample determination part 22 determines whether the data is the quality control data of the first category or the quality control data of the second category (step S2).

Figure 5:
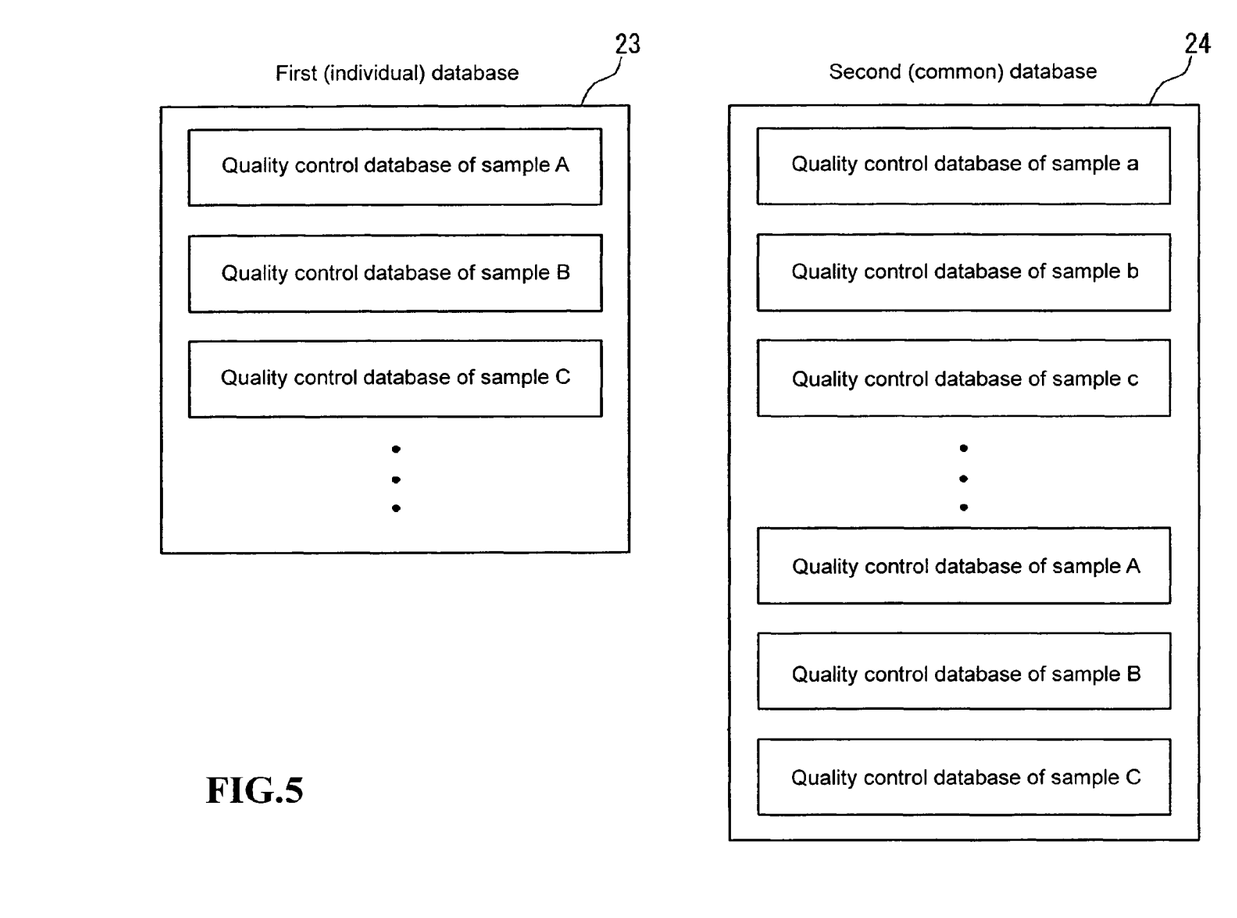
FIG. 5 is a detailed view of a database.

When the data is the quality control data of the quality control sample belonging to the first category, the quality control server 1 accumulates this data in the first database (individual database) 23 (step S3). As shown in FIG. 5, the data is classified for each quality control sample (inspection device), and is accumulated so as to form a population for each sample. Further, the quality control server 1 converts the quality control data of the first category into the data format of the second category (step S4). In addition, the quality control server 1 complements insufficient data as the quality control data to be accumulated in the second database, being the common database as needed (step S4). The data thus converted/complemented is also accumulated in the second database (step S5). As shown in FIG. 5, the data is classified for each sample and is accumulated so as to form an (entire body of) the population for each sample.

When the data is the quality control data of the quality control sample belonging to the second category, the quality control server 1 accumulates this data in the second database 24, being the common database (step S6). As shown in FIG. 5, the data is classified for each sample, and is accumulated so as to form an (entire body of) the population for each sample. As a result of the aforementioned processing, all of the quality control data is accumulated in the common database 24, irrespective of the category. Accordingly, all of the quality control data can be processed by the second statistic processing with abundant functions. In addition, since the quality control data of the first category exists in the first database 23, and the quality control data of the second category exists in the second database 24, the display of the aggregating/quality control results according to the category is easy. Note that the data accumulated in the databases 23 and 24 is processed by the statistic processing part, thus enabling each kind of display by the Web screen.

Figure 6:
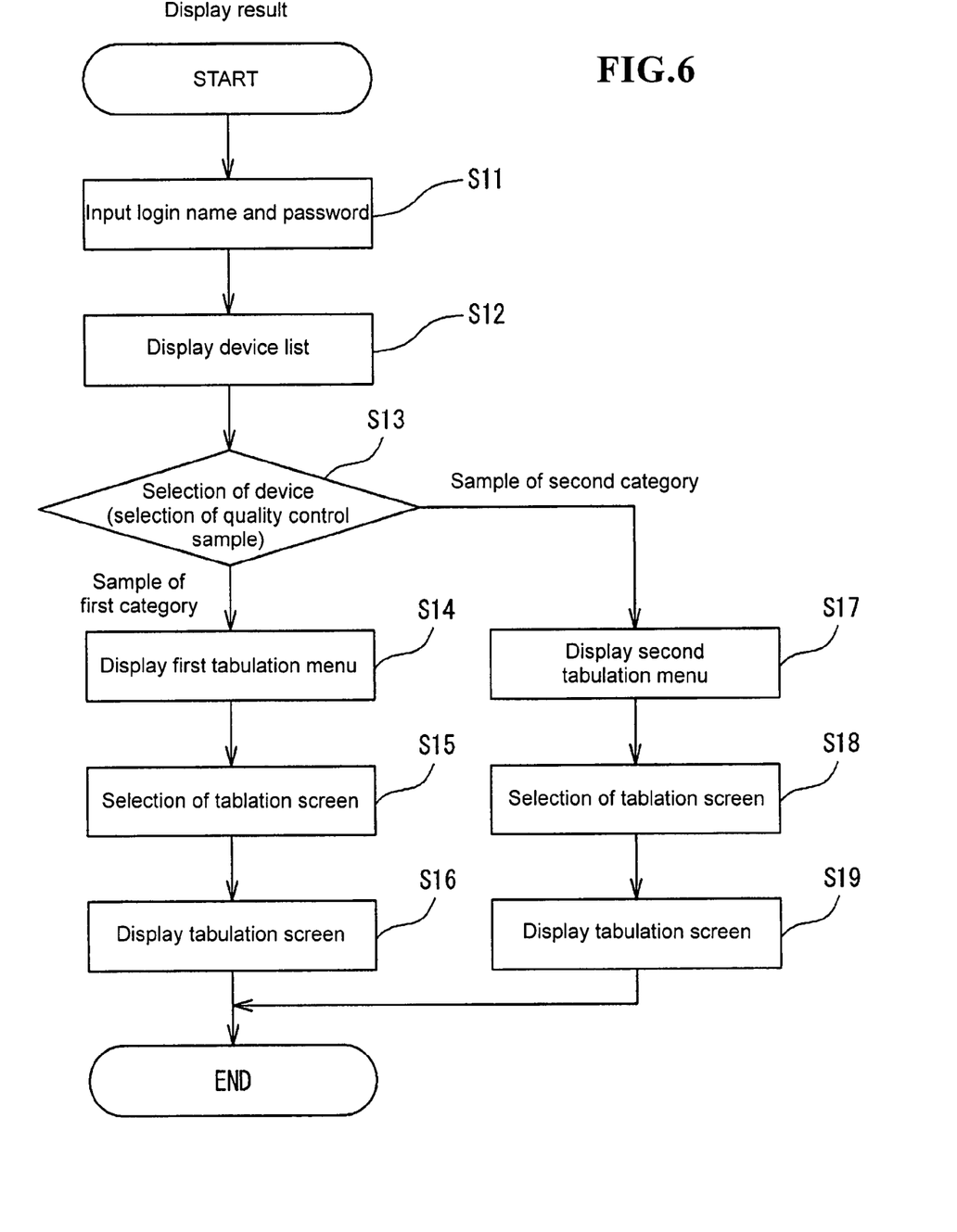
FIG. 6 is a flowchart of a display processing of a quality control result.

FIG. 6 shows a procedure for viewing the quality control result (QC result) by logging-in the quality control server 1 by the user. First, the quality control server 1 receives the input of the login name and the password on the login screen (step S11).

Figure 7:
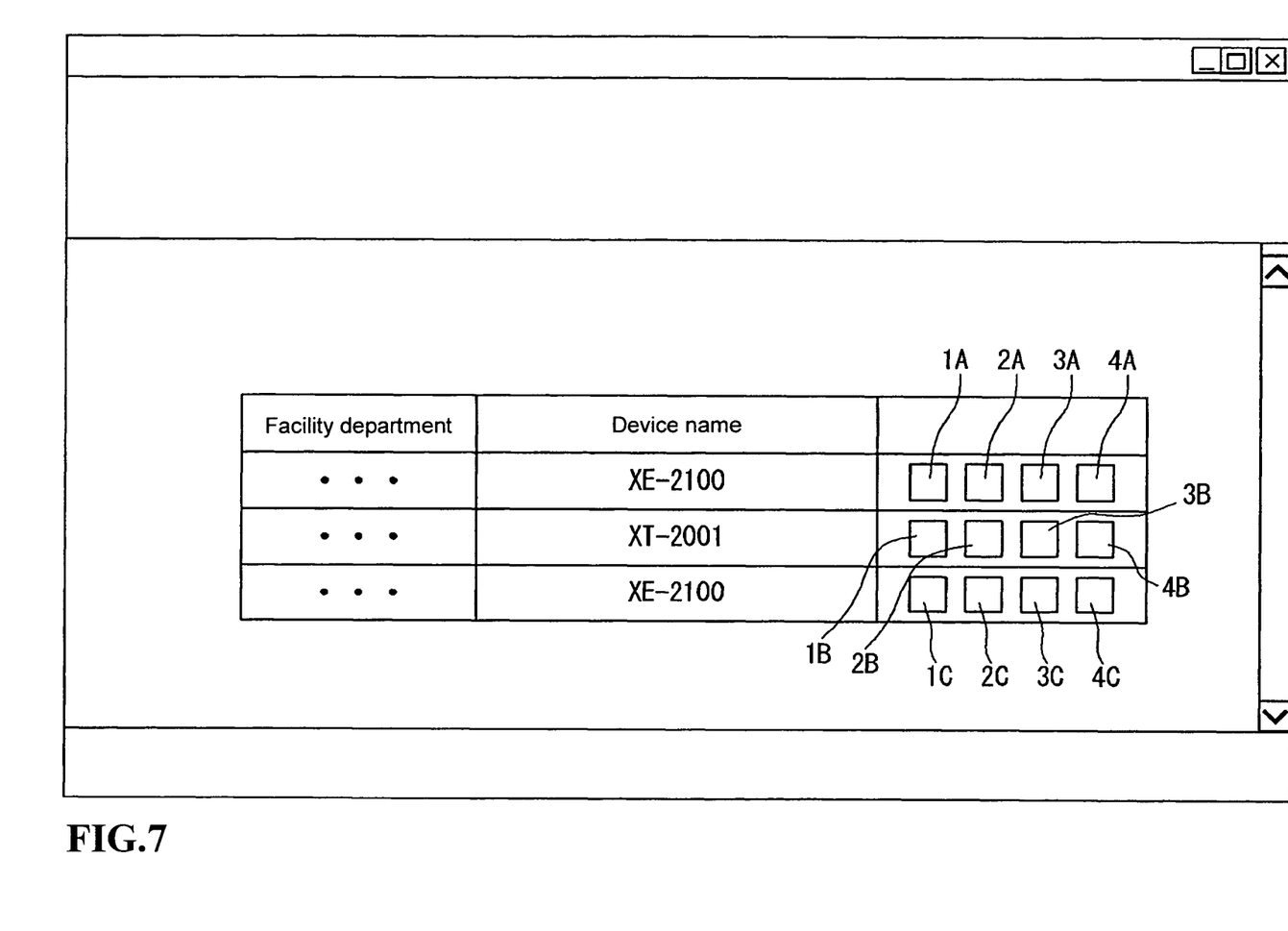
FIG. 7 is a view showing a device list screen.

After authentication success of the login, the display control part 11 of the quality control server 1 refers to the registration information database 14, acquires user attribute information of the user who logs-in (list information of inspection device possessed by user), and displays a list of inspection device possessed by the user registered in the quality control server 1 (step S112). A device list screen is shown in FIG. 7. In the device list screen, the name of a facility department, where the device is installed, is displayed together with the name of the device possessed by the user who logged-in the system. In addition, an operation icon for moving to each kind of screen is displayed for each device. As a screen moving operation icon, there are provided quality control result icons 1A, 1B, 1C for moving to the screen where the operation for displaying the quality control result (QC data) is performed, manual input icons 2A, 2B, 2C for moving to the screen for manually-inputting the quality control data, error history icons 3A, 3B, 3C for moving to the screen for displaying an error history of the device, device information icons 4A, 4B, 4C for moving to the screen for displaying device information such as facility name where the device is installed, device category, device model name, and device serial number. Note that the device list screen of FIG. 7 is commonly used, irrespective of the category of the quality control sample used by the user.

In the device list screen of FIG. 7, when any one of the quality control result icons 1A, 1B, 1C is selected (selection of device; step S13), the quality control server 1 displays a tabulation menu screen (display screen for first category) in accordance with the kind of the device possessed by the user (steps S14 and S17), based on the kind of the selected inspection device. In this quality control server 1, the quality control sample and the inspection device used by the user are corresponded, and by the selection of the inspection device, the user selects the quality control sample used in this inspection device.

Figure 8:
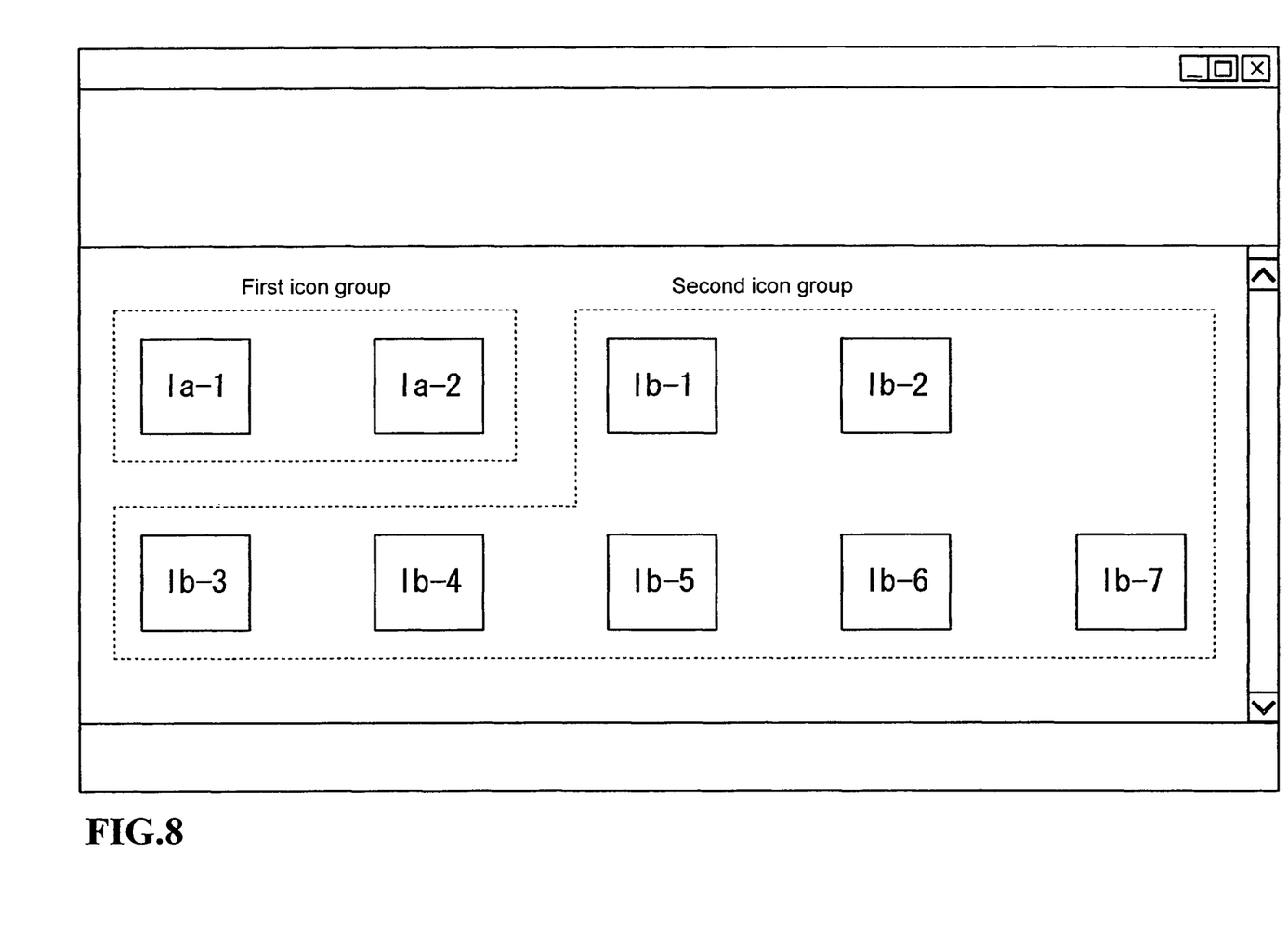
FIG. 8 is a view showing a first tabulation menu screen.

When the quality control sample used by the user belongs to the first category, a first tabulation menu screen as shown in FIG. 8 is displayed (step S14). This first tabulation menu screen has a plurality of operation icons Ia-1, Ia-2, Ib-1, Ib-2, Ib-3, Ib-4, Ib-5, Ib-6, and Ib-7. The operation icons of the first tabulation menu screen are largely classified into two. One of them is a first icon group Ia-1 and Ia-2 for performing a result display after performing the first statistic processing based on the first database 23, and the other of them is a second icon group Ib-1, Ib-2, Ib-3, Ib-4, Ib-5, Ib-6, and Ib-7 for performing a result display after performing the second statistic processing based on the second database 24.

Here, the quality control data of the quality control sample belonging to both categories is accumulated in the second database, and therefore the icons belonging to the second icon group are common operation icons capable of displaying the quality control result for both categories. Namely, all users can display the quality control result by the second statistic processing with abundant functions, irrespective of the kind of the used sample.

Meanwhile, the operation icons belonging to the first icon group are the statistic processing based on the first database 23, and since only the data of the first category is accumulated in the first database, the first icon group is a group for displaying the individual quality control result by an aggregating method (first statistic processing) specific to the quality control sample belonging to a specific category (first category).

The icon Ia-1 of the first icon group is an icon for displaying the quality control result based on the first database. Specifically, when the icon Ia-1 is clicked (step S15), it is possible to display an SDI chart for displaying a state (deviation) of the measurement value with respect to a population statistic value (average value of quality control result) for each sample (device) in a chart per day, and a numerical value table for confirming a numerical value of a result of aggregating and abnormality determination such as the measurement value and a population statistic value and an error flag (step S16). In addition, the icon Ia-2 of the first icon group is an icon for displaying the quality control result prepared by the statistic processing part 26 based on the first database 23 as a business form list that can be downloaded. The icon Ib-1 of the second icon group is an icon for displaying the quality control result, based on the second database 24. Specifically, when the icon Ib-1 is clicked, it is possible to display an SDI chart for displaying a state (deviation) of the measurement value with respect to a selected standard population statistic value (average value of quality control result) in a chart per day, and a numerical value table for confirming the numerical value of the result of aggregating and abnormality determination such as the measurement value, the population statistic value and the error flag. When the SDI chart by the icon Ib-1 is displayed, the standard population group, being a display object, can be selected from the entire body of the population for the same quality control sample. The standard population includes several kinds classified by the classification of inspection, inspection method, inspection device, and inspection sample as factors. When the user selects a desired standard population, the quality control server 1 displays the state of the measurement value with respect to the statistic value of the selected standard population.

The icon Ib-2 of the second icon group is an icon for displaying the quality control result prepared by the statistic processing part 26 based on the second database 24, as the business form list that can be downloaded. Based on the second database 24, the icon Ib-3 of the second icon group is an icon for displaying QAP MATRIX for confirming a disparity between the average value of the device and the average value of the entire body for each inspection item. The icon Ib-4 of the second icon group is an icon for calculating the deviation (SDI) and variation (P1) from intraday, monthly, and daily report values or an aggregating result of the selected two-density quality control samples, and displaying an SDI/PI control chart or a numeric value table. The icon Ib-5 of the second icon group is an icon for displaying the SDI/PI control chart or the numerical table in the group, based on the second database 24. The icon Ib-6 of the second icon group plots self-device data and all-device data in a two-density chart based on the second database 24, and displays a dispersion view for confirming where the data of the self-device is positioned. The icon Ib-7 of the third icon group is an icon for displaying a precision evaluation report, based on the second database 24.

Figure 9:
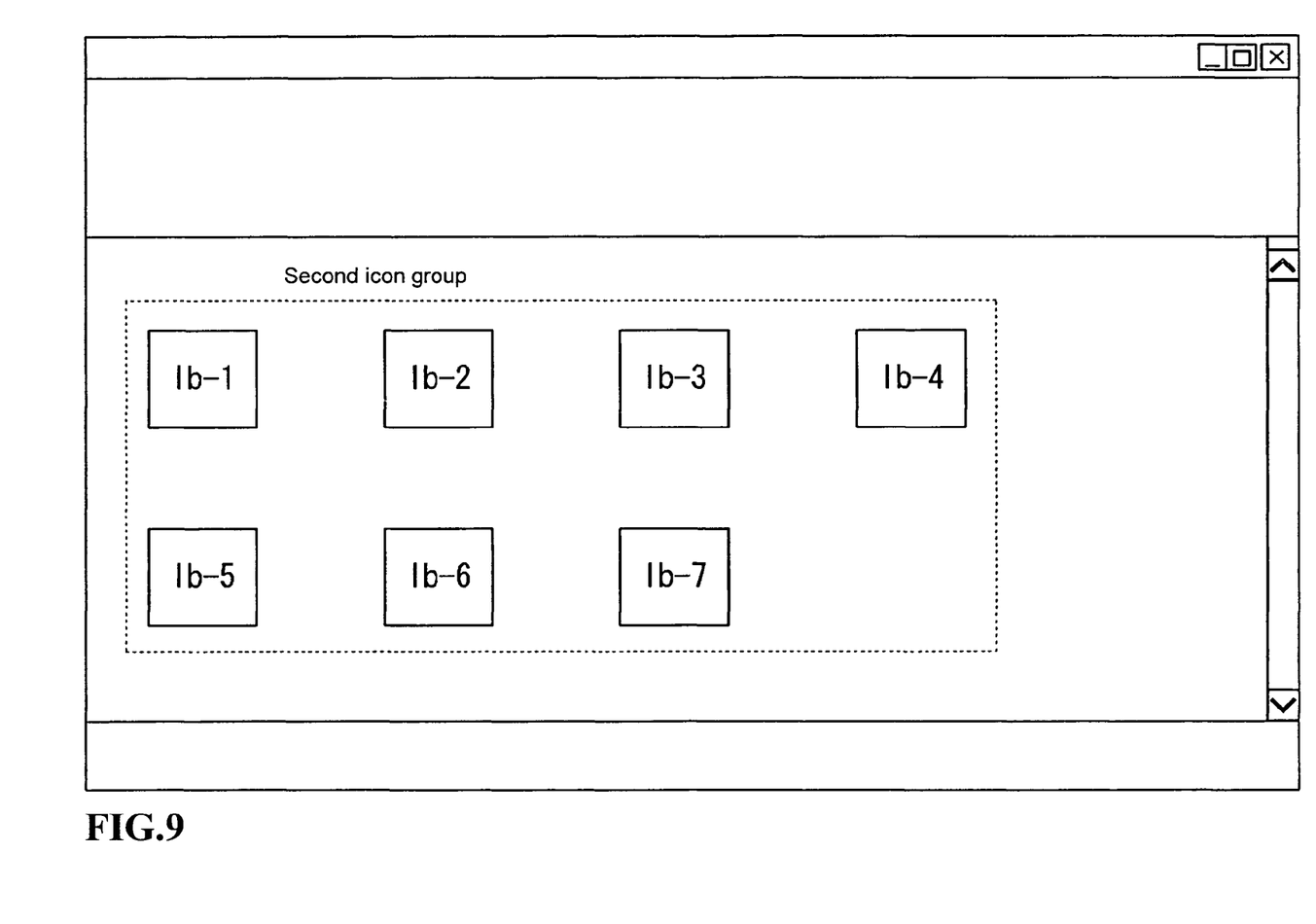
FIG. 9 is a view showing a second tabulation menu screen.

When it is so determined that a determination result of the step S14 belongs to the second category, the display control part 11 displays a second tabulation menu screen as shown in FIG. 9 (step S17). This second tabulation menu screen (display screen for second category (second user)) has a plurality of operation icons Ib-1, Ib-2, Ib-3, Ib-4, Ib-5, Ib-6, and Ib-7, and by selecting these icons (step S18), a screen corresponding to each icon can be displayed (step S19).

In this second tabulation menu screen, only the second icon group in the first tabulation menu screen is displayed. Namely, the user using the quality control sample of the second category can use only the function of the second statistic processing.

In this way, the system of this embodiment can provide the common statistic processing (second statistic processing) to both categories, and therefore convenience of the user is improved.

The present invention is not limited to the aforementioned embodiment. For example, an object for quality control is not limited to the exemplified ones, but can be applied to various ones. Also, the category of the quality control sample is not limited to two, but three or more arbitrary numbers of categories can be provided. In addition, the kind of the statistic processing and the kind of the display screen can be set to arbitrary numbers.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A quality control system, comprising:
user terminals each associated with at least one analyzer; and
a quality control server connected to the analyzers and the user terminals via a network, wherein the quality control server comprises:
a processor; and
a memory operable under control of the processor and comprising a first database and a second database, the memory storing instructions enabling the processor to perform operations comprising:
receiving from a first group of user terminals first sets of measurement information on a first category of control samples run by a first group of analyzers associated with the first group of user terminals, wherein the first category of control samples are correlated to the first group of analyzers;
storing the first sets of measurement information in the first database, wherein the first database comprises identifications of the first category of control samples and measurement results obtained by running the first category of control sample at the first group of analyzers;
receiving from a second group of user terminals second sets of measurement information on a second category of control samples run by a second group of analyzers associated with the second group of user terminals, wherein the second category of control samples are correlated to types of analyses performed by the second group of analyzers;
storing the second sets of measurement information in the second database, wherein the second database comprises identifications of the second category of control samples, the types of analyses and identifications of the second group of analyzers, and wherein the first sets of measurement information are also storable in the second database;
in response to a request from one user terminal, sending a selection screen for display on said one user terminal prompting a selection indicative of either the first control sample category or the second control sample category;
in response to a selection indicative of the first control sample category, calculating first statistical data including a deviation of the measurement result obtained by an analyzer associated with said one user terminal among measurements results obtained by analyzers which run the same control sample in the first category; and
in response to a selection indicative of the second category of control sample, calculating second statistical data including a deviation of the measurement result obtained by an analyzer of said one user terminal, the deviation being calculable among one group of measurement results selectable at said one user terminal from the following groups of measurement results:
(a) measurement results by analyzers which run the same control sample in the second category;
(b) measurement results by analyzers which run the same type of analysis, using the same control sample in the second category; and
(c) measurement results by the same type of analyzers which run the same control sample in the second category.

2. The quality control system of claim 1, wherein the selection screen is displayed as Web screens.

3. The quality control system of claim 1, wherein the operations further comprise:
receiving a login name and a password from a user terminal via a login screen displayed on the user terminal; and
authenticating the user terminal; and
wherein the selection screen is displayed on the user terminal only after the user terminal has been authenticated.

4. The quality control system of claim 1, wherein the operations further comprise:
converting data format of the first sets of measurement information so that the data format conforms to the second database.

5. The quality control system of claim 1, wherein the selection screen lists at least one analyzer associated with said one user terminal for selection of one of the at least one analyzer, wherein a respective at least one analyzer is correlated with one control sample for use therewith.

6. A user terminal connected to a quality control server via a network, the user terminal comprising:
a display device; and
a memory under control of a processor, the memory storing instructions enabling the processor to perform operations comprising:
requesting from the quality control server displaying of a selection screen comprising a first icon corresponding to a first quality control sample which is categorized in a first category and a second icon corresponding to a second quality control sample which is categorized in a second category;
displaying the selection screen on the display device;
receiving an input selecting the first icon or the second icon via the selection screen;
sending to the quality control server the input selecting the first icon or the second icon;
displaying, on the display device, when the input selecting the first icon is sent, a first screen comprising a third icon corresponding to a first quality control result which is obtained, using a first statistical operation, from a plurality of measurement results of the first quality control samples; and
displaying on the display device, when the input selecting the second icon is sent, a second screen comprising a fourth icon corresponding to a second quality control result which is obtained, using a second statistical operation different from the first statistical operation, from a plurality of measurement results of the second quality control samples.

7. The user terminal of claim 6, wherein the selection screen, the first screen, and the second screen are displayed as Web screens.

8. The user terminal of claim 6, wherein the first screen further comprises the fourth icon.

9. The user terminal of claim 6, wherein the first screen comprises the third icon in plural, and wherein the second screen comprises the fourth icon in plural.

10. A quality control server connected to user terminals via a network, comprising:
a processor; and
a memory operable under control of the processor and comprising a first database and a second database, the memory storing instructions enabling the processor to perform operations comprising:
receiving from a first group of user terminals first sets of measurement information on a first category of control samples run by a first group of analyzers associated with the first group of user terminals, wherein the first category of control samples are correlated to the first group of analyzers;

storing the first sets of measurement information in the first database, wherein the first database comprises identifications of the first category of control samples and measurement results obtained by running the first category of control sample at the first group of analyzers;

receiving from a second group of user terminals second sets of measurement information on a second category of control samples run by a second group of analyzers associated with the second group of user terminals, wherein the second category of control samples are correlated to types of analyses performed by the second group of analyzers;

storing the second sets of measurement information in the second database, wherein the second database comprises identifications of the second category of control samples, the types of analyses and identifications of the second group of analyzers, and wherein the first sets of measurement information are also storable in the second database;

in response to a request from one user terminal, sending a selection screen for display on said one user terminal prompting a selection indicative of either the first control sample category or the second control sample category;

in response to a selection indicative of the first control sample category, calculating first statistical data including a deviation of the measurement result obtained by an analyzer associated with said one user terminal among measurements results obtained by analyzers which run the same control sample in the first category; and in response to a selection indicative of the second control sample category, calculating second statistical data including a deviation of the measurement result obtained by an analyzer of said one user terminal, the deviation being calculable among one group of measurement results selectable at said one user terminal from the following groups of measurement results:

(a) measurement results by analyzers which run the same control sample in the second category;

(b) measurement results by analyzers which run the same type of analysis, using the same control sample in the second category; and (c) measurement results by the same type of analyzers which run the same control sample in the second category.

11. The quality control server of claim 10, wherein the selection screen is displayed as Web screens.

12. The quality control server of claim 10, wherein the operations further comprise:

receiving a login name and a password from a user terminal via a login screen displayed on the user terminal; and authenticating the user terminal;

wherein the selection screen is displayed only after the user terminal has been authenticated.

13. The quality control server of claim 10, wherein the operations further comprise:

converting data format of the first sets of measurement information so that the data format conforms to the second database.

14. The quality control server of claim 10, wherein the selection screen lists at least one analyzer associated with said one user terminal for selection of one of the at least one analyzer, wherein a respective at least one analyzer is correlated with one control sample for use therewith.

* * * * *